United States Patent [19]

Maloney et al.

[11] Patent Number: 4,457,711
[45] Date of Patent: Jul. 3, 1984

[54] PRESSURIZED ORAL SPRAYING DEVICE

[76] Inventors: Holly H. Maloney; Albert L. Maloney, both of 16 Rue Grand Vallee, Newport Beach, Calif. 92660

[21] Appl. No.: 365,505

[22] Filed: Apr. 5, 1982

Related U.S. Application Data

[63] Continuation-in-part of Ser. No. 149,002, May 12, 1980, abandoned.

[51] Int. Cl.³ .................................................. A61C 1/10
[52] U.S. Cl. ........................................ 433/82; 128/66; 15/167 R; 222/192; 433/80
[58] Field of Search .................... 433/82, 80, 89, 84, 433/125, 142; 128/62 A, 66; 15/167 R, 167 A, 110; 222/192, 106; D24/63

[56] References Cited

U.S. PATENT DOCUMENTS

| | | | |
|---|---|---|---|
| 1,868,893 | 7/1932 | Gentle | 128/62 A |
| 2,039,278 | 5/1936 | Blanchard | 128/62 A |
| 2,110,315 | 3/1938 | Wolfson | 128/62 A |
| 2,400,912 | 5/1946 | Britt et al. | 433/125 |
| 2,738,528 | 3/1956 | Fridge, Sr. | 433/82 |
| 3,093,857 | 6/1963 | Hersh | 222/192 |
| 3,389,468 | 6/1968 | Lewis et al. | 433/82 |
| 3,480,009 | 11/1969 | Sinai | 128/66 |
| 3,579,835 | 5/1971 | Levenson | 433/82 |
| 3,624,219 | 11/1971 | Perlitsh | 222/192 |
| 4,173,828 | 11/1979 | Lustig et al. | 128/62 A |

FOREIGN PATENT DOCUMENTS 14652 10/1933 Australia ............................... 433/80

Primary Examiner—John J. Wilson
Attorney, Agent, or Firm—George F. Bethel; Patience K. Bethel

[57] ABSTRACT

The following specification discloses an oral hygienic spraying device. The oral hygienic spraying device comprises a material that can be used for oral hygiene disposed within a pump container or pressurized metal bottle having a spring actuated valve that allows for release of the pressurized hygienic material in the form of a spray or mist. The spray or mist is released when the pump or valve is depressed, through a scrubbing cup. The scrubbing cup has a plurality of radially disposed members within the cup for purposes of abrading and scrubbing residue such as plaque, food materials, and the foreign substances from the teeth and gums of a user. The scrubbing cup can be formed as part of the top or head of the oral spraying device so that it sits over the exit from the valve, or it can be separately attached to a valve connection fixture. The foregoing provides for the utilization of a spray for oral hygiene, as well as a scrubbing of foreign substances on the teeth or gums so that a combination removal and hygienic flushing is accomplished.

2 Claims, 9 Drawing Figures

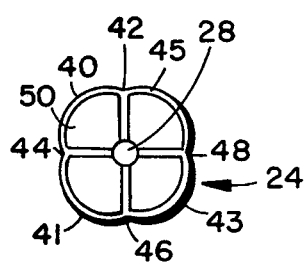
FIG. 3
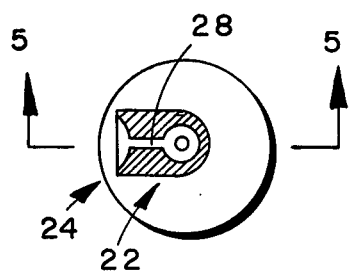
FIG. 2
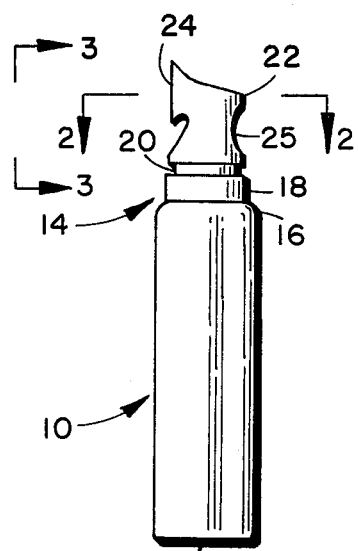
FIG. 1
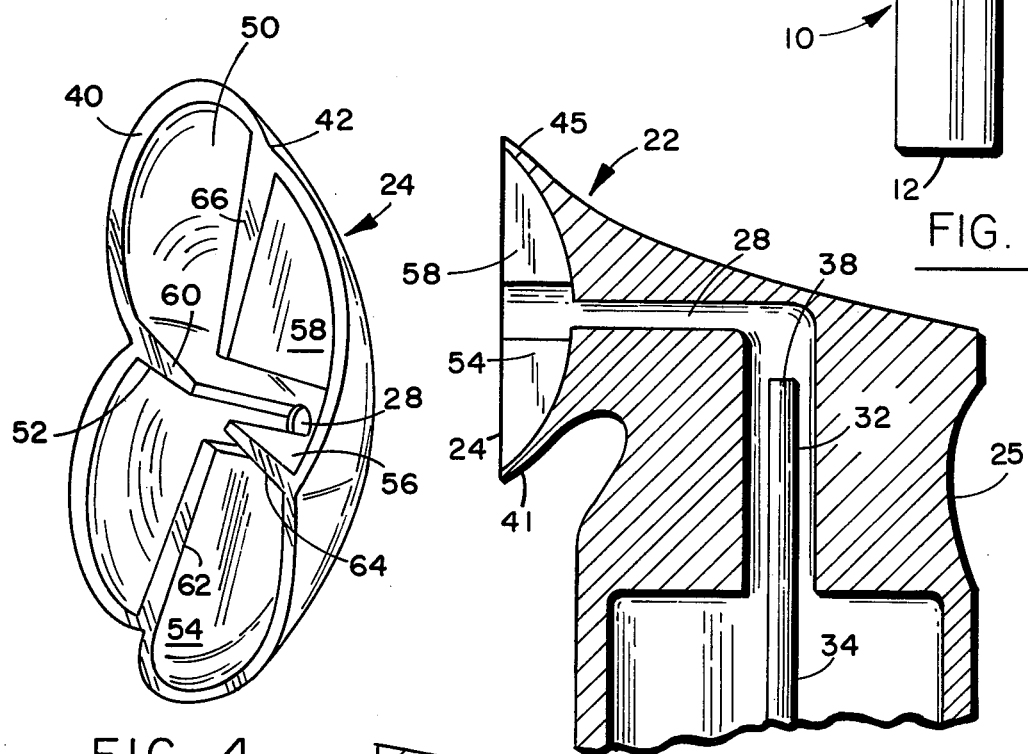
FIG. 4
FIG. 5
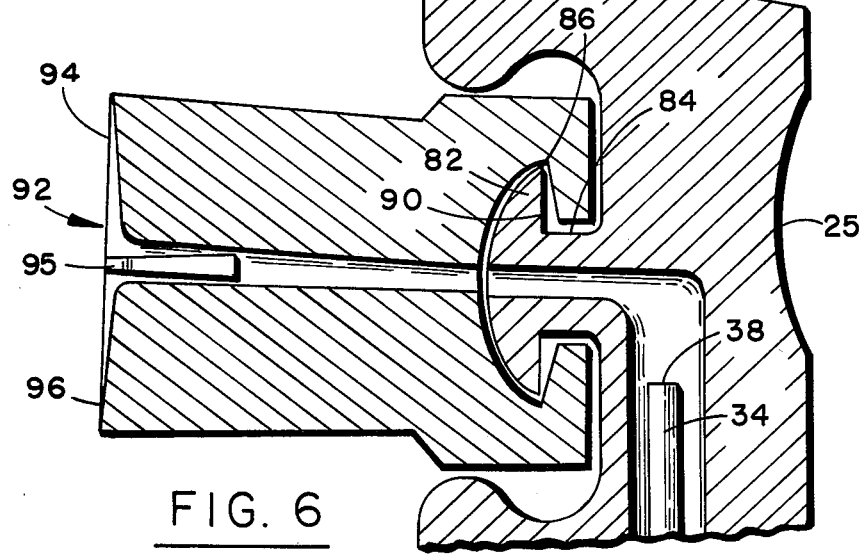
FIG. 6

PRESSURIZED ORAL SPRAYING DEVICE

This case is a continuation-in-part of our previously filed case for a pressurized oral spraying device, bearing Ser. No. 149,002, filed May 12, 1980, now abandoned

BACKGROUND OF THE INVENTION

1. Field of the Invention

The field of this invention lies within the oral hygiene art. More particularly, it lies within the oral spray and mist art wherein an oral hygienic spray or solution is introduced into the oral cavity for purposes of oral hygiene, and breath freshening.

2. The Prior Art

The prior art with regard to oral hygiene has involved the utilization of oral sprays, mouthwashes, solutions, and mouth rinses, all generally in a solution. The solution is introduced into the mouth, either through a proportionalized mixture from a stronger solution mixed with water, to provide a weaker solution, or is directly introduced in its full strength into the mouth. Lately it has been common to utilize a hygienic spray or mist sprayed directly into the mouth. The spray is contained within a pressurized bottle. The pressurized bottle has the oral hygienic solution pressurized by a gas, so that it can be sprayed from an opening of the bottle.

The bottle generally has a compressible pump or actuator that is connected to a valve. The valve allows for the release of the gas and oral hygienic solution in the form of a spray sol or mist. The net result is one providing an oral hygienic spray solution within the mouth, along with a breath freshening effect.

One of the drawbacks of the prior art is that the oral spray does not necessarily remove embedded or extraneous material on the surface of the teeth or the gums of the user. In effect, a spray can only be used as a rinse, or a freshener in an attempt to override any extraneous odors and cannot be used to remove extraneous material that causes such odors and tooth decaying residue, such as bacterial plaque.

This invention incorporates a unique and separate scrubbing device that is handy and capable of being used in combination with the spray. The scrubbing device is a cup-shaped member that can be formed at its edges to scrub the gums and the gum regions. In addition thereto, the cup-shaped device has a plurality of ribs interiorly thereof or narrow walled members that provide for an abrading or scrubbing effect when the cup-shaped member is moved backwardly and forwardly across the surfaces of the teeth. In particular, the ribs are made of a flexible elastomeric material that scrub or abrade when they are pressed against the surface of the teeth. The scrubbing or abrading when the ribs are depressed against the surface of the teeth, causes a removal of extraneous plaque, food particles, and surface accumulations on the teeth. At the same time the foregoing scrubbing action is taking place, a rinsing or irrigation of the material is enhanced by the spraying of the oral hygienic spray.

The foregoing combination of the cup-shaped scrubber and the oral spray overcomes the deficiencies of the prior art by providing a portable unique spraying device in combination with a scrubbing means at the spray head thereof. Thus, a physical scrubbing or removal of bacterial plaque can take place while at the same time an oral spray or solution can be applied for flushing the area. This serves to irrigate the gum area and oral cavity for removal of the scrubbed extraneous material, and bacterial plaque, while at the same time freshening the entire oral cavity.

SUMMARY OF THE INVENTION

In summation, this invention comprises a combination oral mist and spraying bottle with a cup-shaped scrubber having radial ribs around the interior thereof.

More particularly, the invention comprises a pressurized bottle of oral solution. The oral solution is pressurized by a gas therein or a pump for driving the solution in spray or mist form. The bottle has a valve therein with a conduit leading from the valve. The conduit and valve combination can be operated by depressing the top of the bottle. The top of the bottle incorporates a head having a cup-shaped scrubbing conformation, that is detachable or removable therefrom.

The top of the bottle with the cup-shaped scrubbing combination serves to abrade or eliminate residue and bacterial plaque on the teeth of a user. This is accomplished through a plurality of radial ribs for abrading purposes within the cup-shaped member. The radial ribs or abrading surfaces within the cup-shaped member impinge against the teeth or gums of a user so that the edges thereof perform a scrubbing function to remove the residue and problem causing bacterial plaque from the teeth.

The foregoing abrading ribs and cup-shaped member for scrubbing the mouth of a user, adjacent to the gum line, is enhanced by an oral spray. The oral spray helps to loosen or remove deleterious material and plaque through an irrigation or spraying. The oral hygienic spray incorporates an antiseptic material, as well as a breath freshening material.

The entire combination thus provides for a scrubbing and abrading removal of residue and bacterial plaque on one's teeth and gums, while providing for antiseptic irrigation and freshening of the oral cavity.

BRIEF DESCRIPTION OF THE DRAWINGS

The invention will be more clearly understood by reference to the description below taken in conjunction with the accompanying drawings wherein:

FIG. 1 shows a side elevation view of the oral spraying and scrubbing device of this invention;

FIG. 2 shows a sectional view looking downwardly in the direction of lines 2—2 of FIG. 1 wherein the oral scrubbing head is shown in its midline sectional view through the intermediate portion thereof;

FIG. 3 shows a frontal view of the oral scrubbing cup of this invention looking in the direction of lines 3—3 of FIG. 1;

FIG. 4 shows a perspective view of the oral scrubbing cup with four radial ribs surrounding an opening thereof;

FIG. 5 shows a midline sectional view looking in the direction of lines 5—5 of FIG. 2 which shows the section of the head of the oral scrubbing device;

FIG. 6 shows an alternative scrubbing head that can be attached to the head of an oral spray bottle through the connection shown therein;

DESCRIPTION OF THE PREFERRED EMBODIMENTS

Figure 7:
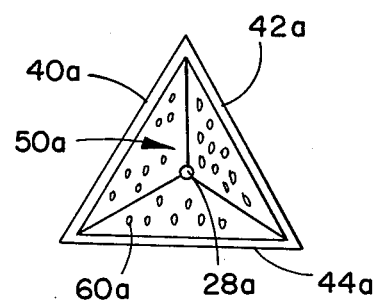
FIG. 7 shows a second alternative scrubbing head formed as a triangular concave member having scrubbing protuberances on the inner surface thereof.

Looking more particularly at FIG. 1 and the figures ancillary thereto, namely FIGS. 2 through 5, it can be seen that a bottle 10 has been shown. The bottle 10 comprises a metal cannister or container having a base 12 and a neck portion 14. The neck portion turns over at curved surface 16 and terminates in an upstanding neck 18.

The upstanding neck 18 receives a sleeve 20. The sleeve 20 has a cap 22 thereover. The cap 22 is formed with a cupped frontal area 24, and a finger indentation 25 for scrubbing action.

Figure 9:
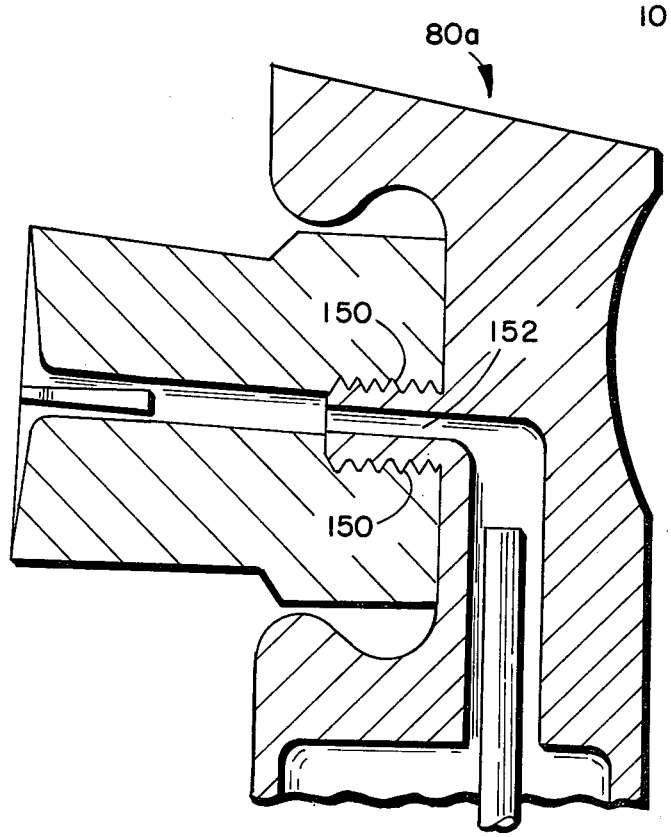

The cupped frontal area 24 is formed as an entire portion of the cap 22 or can be formed separately as in FIGS. 6 and 9. The cap 22 overrides a plunger or other valve actuating means within the sleeve 20. In addition thereto, the sleeve 20 can also be utilized for providing a telescoping actuation means.

The bottle 10 has pressurized contents comprising an oral hygienic solution. The contents are internally pressurized by a gas that drives the contents out of the bottle when a valve is actuated. The oral hygienic solution is sprayed in a colloidal suspension, spray, or mist that can also be an aerosol or sol when sprayed or released from its internally pressurized state within the bottle 10.

The internally pressurized contents in the bottle 10 emanate through the front of the cup-shaped member 24 through an opening 28 in the base thereof as a mist or spray.

The opening 28 is in direct connection to a passage which turns ninety degrees and leads to a second passage 32 within the cap 22. Within the passage 32, an upstanding conduit 34 is shown. The upstanding conduit 34 is directly connected into the container 10. The connection is through a valve inbetween the conduit 34 and the interior of the container 10. The valve is actuated when the cap 22 is depressed which causes the depression of the sleeve or collar 20. Also, the cap 22 can be directly connected to a linkage means of any type in order to actuate a valve so that the pressurized contents of the oral hygienic spray can be released through the conduit 34 at its opening 38. The depression of the cap 22 thereby releasing the spray through the opening 38 is effectuated by downward depression of the member 22. The spray then emanates out of the opening 28 into the cup-shaped member 24.

The entire head or cap 22 can be of varied form of resilient material such as a silicon rubber, plastic polymer, or a resilient elastomeric or plastic material that will provide for flexibility with relieved surfaces to scrub a user's teeth, as will be expanded upon hereinafter. Regardless of the foregoing, the material should be of a durameter sufficiently soft to allow the cup-shaped member 24 to collapse into a flatter configuration to permit scrubbing without undue abrasion against the user's gums.

The valve function of the container 10 can be provided by any suitable valving member, whether it be of the type utlized in existing pressurized oral spray applicators or other aerosol type valves. It is well known that aerosol type valves are easily obtained for usage by actuation through the cap 22, sleeve 20, or neck 18. In addition thereto, existing type spray containers can be utilized by incorporating a substituted cap 22 for operatively actuating the valve, while at the same time providing the functions of spraying and abrading removal of residue and bacterial plaque on a user's teeth.

The cup 24 has an outlying periphery 40 formed as four arcuate members terminating and joined in four inwardly extending terminal points 42, 44, 46 and 48. The arcuate members 40, 41, 43, and 45 can be formed as a completely circumferential and round walled cup, eliminating the depressions 42 through 48. Additionally, other conformations can be utilized, so long as a depressed configuration having relieved surfaces provided by protuberances substituted for ribs, are provided. The primary object is to have resilient or peripheral walls analogous to walls 40 through 45, wherein an inner depression analogous to depression 50 is formed with relieved surfaces therein. For instance, a rectangular, rounded or triangular peripheral conformation with interior ribs, bumps or protuberances having depressions, such as shown in FIG. 7, can be utilized.

To provide for the depressions 50 and the relieved surfaces, four walls 52, 54, 56 and 58 are radially arranged around the opening 28 which can be greater in number. However, there should be sufficient room between the walls to allow at least a partial collapse of the walls into the space therebetween to avoid undue surficial buildup. The four walls 52 through 58 have upper surfaces respectively 60, 62, 64 and 66, which provide a scrubbing function to the sufaces upon which they impinge or abrade. The walls 52 through 58 serve to provide scrubbing or abrading surfaces when moved over the surface of the teeth to effectuate removal of residue and plaque. The indentation 25 allows one's fingers to seat against the cup to provide scrubbing force and control.

The edges 40 through 45 allow for an insertion of the elastomeric peripheral edges of the cup 34 against the gum line and into the gum line area for helping to remove extraneous material between the gum and the teeth. At the same time, when the cup 24 is pushed into a flatter conformation, the walls 52 through 58 or protuberances provide a scrubbing function when moved backwardly and forwardly over the surface of the teeth. When the cap 22 is actuated, it allows an irrigation or spray through the opening 38 of the conduit 34 so that it can be conducted out of the opening 28 into a user's mouth between the plurality of walls 52 through 58. The entire function of the device is thereby combined, forming a flexible scrubber with protuberances and an oral irrigator.

The cup 24 can be of any type of resilient plastic or elastomeric material, so long as it does not act in a sufficiently stiff manner to damage the gums. The durameter of the elastomer or plastic should be sufficiently soft to allow a flattening of the cup into a relatively flattened configuration to provide exposure of the ribs and a scrubbing function thereof. When accordingly flattened, the softness of the material will lessen gum damage.

In addition thereto, the walls 52 through 58 can be formed as a plurality of radially extending members in a completely symmetrical cup. The radial members can be of any suitable conformation and can be depressed slightly below the surface of the walls 40 through 45, or elevated, depending upon the type of scrubbing action that is desired. The walls and entire cup should have the same flattening capabilities as the prior described ribs. Also, the material within the container 10 can be varied to incorporate any particular type of oral hygienic spray or breath freshener. Suffice it to say, numerous conformations incorporating the plural scrubbing walls, the cup-shaped configuration and internally pressurized atomized sprayer can be combined.

The showing of FIG. 6 is of a head 80 having a conduit 34 like the foregoing described conduit, and an opening 38. The head 80 is formed with a mushroom-shaped member 82 having an undercut 84 therearound. The mushroom-shaped member receives a frontally belled-out cup 86 having a latching flange in surrounding circumferential relationship so that it can engage the bottom surface 90 of the mushroom-shaped member 82. The flange undercut belled member 86 terminates in a cup-shaped portion 92 forming a cup having walls 94 and 96 that are shown, analogous to walls 52 through 58. The plurality of scrubbing walls 52 through 58 are analogous to walls 94 and 96. Also, second walls, one of which is not shown, are incorporated in bilaterally symmetrical relationship ninety degrees away from each of the walls 94 and 96 on a plane passing therebetween. The one wall shown is designated by numeral 95. Thus, four walls are utilized within the cup-shaped member 92 to provide the scrubbing function analogous to the foregoing described walls 52 through 58. These walls are also of sufficiently soft durameter to allow a flattening of the entire cup-shaped member.

The entire cup-shaped member 92 having the undercut flange 86 can be inserted over the mushroom member 82 and removed at will by a gentle impressing thereover and then a later removal by pulling the elastomeric material over the undercut 86 of the mushroom-shaped member 82.

The foregoing allows for multiple types of scrubbing cups 92 to be applied to a spraying container 10, as well as converting existing containers having a mushroom-shaped attachment member 82.

A further alternative embodiment of FIG. 7, as previously referred to, incorporates a passage or opening 28a, analogous to opening 28. The outer peripheral walls 40a, 42a and 44a circumscribe an interior depressed area 50a. A plurality of raised protuberances 60a form the scrubbing function of the walls as previously described. Thus, the cup 24 can be formed having any particular outer wall with inner scrubbing protuberances of a resilient material that will not damage the gums of a user.

Figure 8:
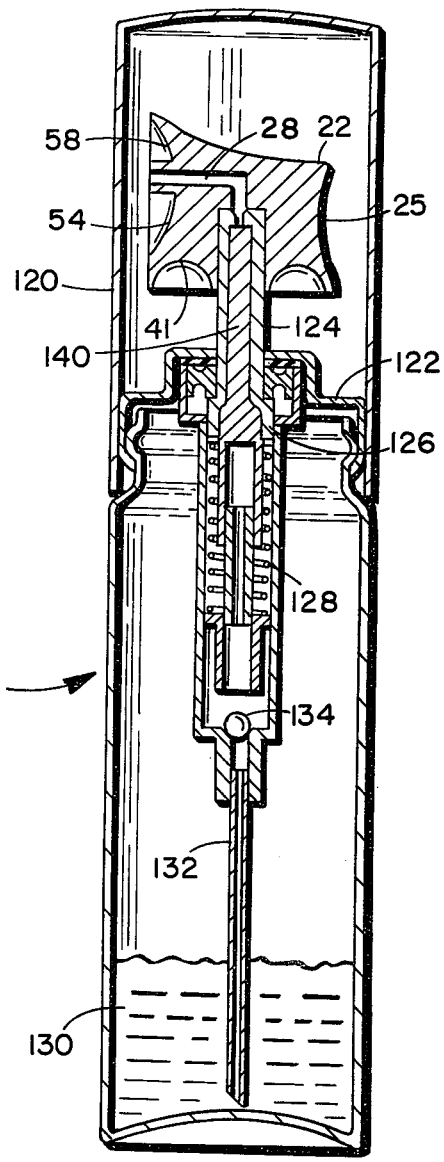
FIG. 8 shows a cross section of the pump operated spray embodiment of this invention; and, FIG. 9 shows a cross section of a head of this invention utilizing a screw fitting for securing the scrubbing head to the body of the spraying apparatus.

Looking at FIG. 8 it can be seen that a container 10 has been shown with a cap 120 thereover. The cap is secured by having a metallic frictional spring character to it that snugly engages a top portion 122 of the container 10. The top of the container has a plunger 124 connected to a head similar to that shown in FIG. 5. The head 22 has the same configurations with a conduit 28 and the outlet similar to that of FIG. 5. The head 22 on the stem 124 causes a plunger 126 to be depressed when it is pushed downwardly. The plunger is on a spring bias provided by a coil spring 128. The foregoing action allows for fluid 130 to be pumped through a conduit 132 by virtue of a ball check valve 134.

The entire configuration thereby allows for flow of fluid outwardly through the conduit which is connected to the lower conduit 140 within the plunger 124.

Thus, when the head 22 is depressed, it causes a spraying of the fluid 130 therethrough in the way of a mist which allows for the scrubbing and removal of the bacterial plaque as set forth hereinbefore.

Looking more particularly at FIG. 9, it can be seen that an alternative attachment has been shown for a head 80a analagous to the head 80. In place of the mushroom undercut of FIG. 6, threads 150 are shown threaded to interior threads 152 of the scrubbing head analogous to that of FIG. 6. Thus, in this embodiment, a removal of the scrubbing head is easily accomplished by merely unthreading the scrubbing head with its interior threads with those of the exterior threads of member 80a.

In addition to the foregoing, the conduit or opening 28 can be offset from the axis or can be provided as plural openings through the cup.

As can be seen from the foregoing, various alternatives and embodiments can incorporate the basic idea of a cup-shaped, concave, or depressed member 24 incorporating a number or ribs, radial walls, or protuberances in combination with a pressurized bottle of spray 10. As a consequence, this invention should be read broadly in light of the claims attendant herewith.

We claim:
1. An oral hygienic device comprising:
 a container of internally pressurized gaseous material having an oral hygienic material therein so that when said gaseous and hygienic material are released, they will form an orally hygienic spray by said gaseous material driving said oral hygienic material therefrom;
 an opening within said container;
 a valve operatively implaced within said opening for controlling the release of the internally pressurized spray from said container;
 a cap attached to said valve in connected relationship thereto for passage of spray when said valve is opened by said cap;
 a resilient concave member formed of silicon rubber having arcuate peripheral upstanding walls terminating at respective points along the outer periphery surrounding the concavity and attached to said cap with an opening connecting to said valve for receiving hygienic material therefrom when said valve is opened; and,
 a plurality of ribs extending from the peripheral upstanding walls inwardly toward the center of said concave member having upper surfaces capable of being exposed for scrubbing purposes in conjunction with said peripheral upstanding walls, said ribs being spaced sufficiently to allow them to resiliently flex into the spaces between them while at the same time permitting the release of spray from between said ribs and of a sufficient softness to allow the concave member to substantially flatten when implaced against a user's teeth, and wherein said plurality of ribs project from the termination points of said peripheral walls.
2. The hygienic device as claimed in claim 1 wherein: said radial ribs at the periphery of said outer wall are fundamentally coplanar in their exposed surface areas.

* * * * *